United States Patent [19]

Wolf et al.

[11] Patent Number: 4,870,100
[45] Date of Patent: Sep. 26, 1989

[54] PYRETHROIDS AND THEIR USE FOR CONTROLLING PESTS

[75] Inventors: Bernd Wolf, Mutterstadt; Hans Theobald, Limburgerhof; Rainer Becker, Bad Durkheim; Norbert Goetz, Worms; Walter Himmele, Walldorf; Rudolf Kropp, Limburgerhof, all of Fed. Rep. of Germany

[73] Assignee: BASF Aktiengesellschaft, Ludwigshafen, Fed. Rep. of Germany

[21] Appl. No.: 940,649

[22] Filed: Dec. 11, 1986

[30] Foreign Application Priority Data

Dec. 31, 1985 [DE] Fed. Rep. of Germany ....... 3546371

[51] Int. Cl.$^4$ .................... A01N 53/00; C07D 307/54
[52] U.S. Cl. .................... 514/461; 514/444; 514/471; 549/60; 549/330; 549/483; 549/488; 549/491; 549/496; 549/497; 549/500; 549/501
[58] Field of Search ...................... 514/444, 461, 471; 549/60, 330, 496, 499, 500, 501

[56] References Cited

U.S. PATENT DOCUMENTS

| | | | |
|---|---|---|---|
| 3,465,007 | 9/1969 | Elliott | 549/497 |
| 3,567,740 | 3/1971 | Matsui et al. | 549/499 |
| 3,673,215 | 6/1972 | Vollrath et al. | 260/232.2 R |
| 4,024,162 | 5/1977 | Elliott et al. | 260/347.4 |
| 4,299,839 | 11/1981 | Omura et al. | 549/499 X |
| 4,327,109 | 4/1982 | Mizutani et al. | 549/499 X |
| 4,332,815 | 6/1982 | Engel | 549/499 X |
| 4,344,961 | 8/1982 | Schwarz et al. | 424/285 |
| 4,379,163 | 4/1983 | Piccardi et al. | 549/499 X |
| 4,431,668 | 2/1984 | Katsuda et al. | 549/491 X |
| 4,622,337 | 11/1986 | Elliott et al. | 514/461 |

FOREIGN PATENT DOCUMENTS 7135872 3/1968 Japan .
5017323 7/1978 Japan .

OTHER PUBLICATIONS

M. Elliott, A. Farnham, N. Janes and P. Needham, "Insecticidal Activity of the Pyrethrins and Related Compounds, III. Methyl-Alkenyl-, and Benzylfurfuryl and -3-furylmethyl Chrysanthemates," Pestic Sci., 5 (1974), 491-496.

M. Elliott, N. Janes and B. Pearson, "The Pyrethrins and Related Compounds XIII, Insecticidal Methyl-Alkenyl and Benzyl-Substituted Furfuryl and Furylmethyl Chrysanthemates", Pestic. Sci., 2 (1971), 243-248.

Primary Examiner—Richard L. Raymond
Attorney, Agent, or Firm—Keil & Weinkauf

[57] ABSTRACT 2-benzylfuryl compounds of the general formula I

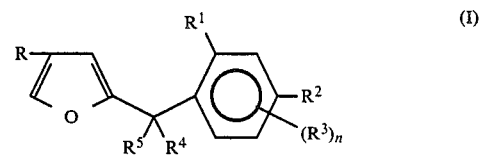

where $R^1$, $R^2$ and $R^3$ are identical or different substituents and are each hydrogen, halogen, alkyl, haloalkyl, alkoxy, haloalkoxy, haloalkylthio, alkenyl or haloalkenyl, each of not more than 6 carbon atoms, n being 1, 2 or 3 where $R^3$ is not hydrogen, and $R^4$ and $R^5$ are each hydrogen or alkyl of not more than 6 carbon atoms, R is —CHO or CHR$^6$OA, R$^6$ is hydrogen, cyano, alkyl, alkenyl, haloalkenyl or alkynyl, each of not more than 6 carbon atoms, or carboxamide, and A is either hydrogen or a radical of an acid typical for pyrethroids, with the proviso that $R^2$ is not hydrogen, chlorine, bromine, methyl or methoxy when $R^1$ is hydrogen or methyl and $R^3$ and A are each hydrogen, and furthermore with the proviso that $R^1$ and $R^2$ are not methyl when A is a radical of tetramethylcyclopropanecarboxylic acid, and finally with the proviso that $R^2$ is not methyl, chlorine, bromine or methoxy and $R^1$ and $R^3$ are not hydrogen when A is a radical of chrysanthemumic acid, their preparation and their use as intermediates for crop protection agents or as crop protection agents.

4 Claims, No Drawings

PYRETHROIDS AND THEIR USE FOR CONTROLLING PESTS

The present invention relates to novel pyrethroids, ie. esters of benzylfurylcarbinols, processes and intermediates for their preparation, pesticides which contain these esters as active ingredients, and methods of controlling pests with these active ingredients.

It is known that certain active ingredients, ie. esters of benzylfurylcarbinols, which are referred to as pyrethroids, are useful for controlling insects (cf. South African Patent Application No. 67/5027; Pestic. Sci. 2 (6), 243; ibid. 5 (4), 491; Japanese Patent Publication Nos. 71/35872 and 80/17323.

We have found novel esters, the intermediates required for their preparation and processes for obtaining the intermediates, which have notable advantages over the known active ingredients and the synthesis steps leading to them.

The esters and their intermediates are of the general formula I

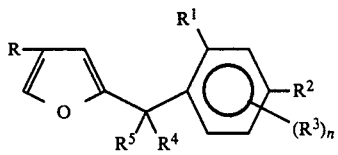

where $R^1$, $R^2$ and $R^3$ are identical or different substituents and are each hydrogen, halogen, alkyl, haloalkyl, alkoxy, haloalkoxy, haloalkylthio, alkenyl or haloalkenyl, each of not more than 6 carbon atoms, n being 1, 2 or 3 where $R^3$ is not hydrogen, and $R^4$ and $R^5$ are each hydrogen or alkyl of not more than 6 carbon atoms, R is —CHO or $CHR^6OA$, $R^6$ is hydrogen, cyano, alkyl, alkenyl, haloalkenyl or alkynyl, each of not more than 6 carbon atoms, or carboxamide, and A is either hydrogen or a radical of an acid typical for pyrethroids, with the proviso that $R^2$ is not hydrogen, chlorine, bromine, methyl or methoxy when $R^1$ is hydrogen or methyl and $R^3$ and A are each hydrogen, and furthermore with the proviso that $R^1$ and $R^2$ are not methyl when A is a radical of tetramethylcyclopropanecarboxylic acid, and finally with the proviso that $R^2$ is not methyl, chloride, bromine or methoxy and $R^1$ and $R^3$ are not hydrogen when A is a radical of chrysanthemumic acid.

The esters of the formula I can be obtained in a conventional manner by reacting carboxylic acids AOH typical for pyrethroids with the benzylfurylcarbinols of the formula I.

Instead of the carboxylic acids, the corresponding acyl halides or, if necessary, the anhydrides, may be used.

Hence, the nature of the intermediates and their availability are important with regard to the invention. In this respect, the following may be stated specifically.

It is known that benzylfurylcarbinols, eg. 2-benzyl-4-hydroxymethylfuran, are a component of synthetic pyrethrum active ingredient [Wegler, Chemie der Pflanzenschutz- und Schädlingsbekämpfungsmittel, Vol. 7 (1981)]. However, it is surprising that, in contrast to the acid component, variation of the benzylfurylcarbinols by substitution of the benzyl radical has remained restricted to only a few examples (Pestic. Sci. 2 (6), 243; Japanese Published Application Nos. 71/35872 and 71/04198; South African Patent Application No. 67/5027).

It is an object of the present invention to provide novel furylcarbinols in order to obtain the abovementioned esters. These furylcarbinols are of the general formula Ia

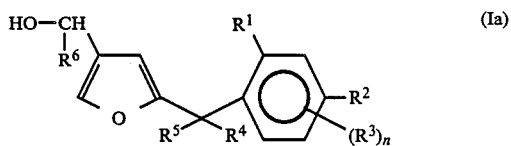

where $R^1$, $R^2$ and $R^3$ are identical or different and are each hydrogen, halogen, alkyl, haloalkyl, alkoxy, haloalkoxy, haloalkylthio, alkenyl or haloalkenyl of not more than 6 carbon atoms, n being 1, 2 or 3, $R^4$ and $R^5$ are each hydrogen or alkyl of not more than 6 carbon atoms and $R^6$ is hydrogen, cyano, alkyl, alkenyl, haloalkenyl or alkynyl of not more than 6 carbon atoms or a carboxamide group, with the proviso that $R^2$ is not hydrogen, chlorine, bromine, methyl or methoxy when $R^1$ is hydrogen or methyl and $R^3$ is hydrogen.

Regarding the preparation of the carbinols, the following may be stated specifically.

Although it is known that furans can be prepared from 1,4-diketones by cyclization [Comprehensive Heterocyclic chemistry 4 (1984), 657 et seq.], 2,4-disubstituted furans are particularly difficult to obtain owing to a lack of the appropriate starting materials. For this reason, various processes have been recommended even for the preparation of the simplest compound, ie. 2-benzyl-4-hydroxymethylfuran (Elliott, Janes and Pearson, J. Chem. Soc. C, 1971, 2551; German Laid-Open Application DOS 2,122,823; Wegler, Chemie der Pflanzeschutz- und Schädlingsbekämpfunssmittel, Vol. 7, page 76 and the literature cited there). However, all these processes have serious disadvantages (multistage synthesis with moderate overall yield, safety problems as a result of high temperatures, isomer formation).

We have found that this object is achieved, and that the furylcarbinols of the general formula Ia, where $R^6$ is hydrogen, can advantageously be obtained if an appropriate isoxazoline of the general formula II is hydrogenated and, if required, the product is treated with an acid

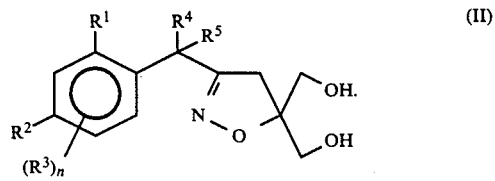

Depending on the specific procedure, this may be effected directly or the hydroxyketone III may be isolated as an intermediate and the desired furylcarbinol obtained in a subsequent step

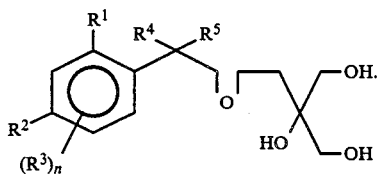
(III)

The catalytic hydrogenation is carried out under the usual conditions. Suitable catalysts are all metals of subgroup 8 in finely divided form, on a carrier or in the form of a compound. Mixtures may also be used. Platinum(IV) oxide has proven particularly useful.

Suitable solvents are ethers (eg. tetrahydrofuran or dioxane), alcohols (eg. methanol or ethanol), nitriles (eg. acetonitrile or propionitrile) and ketones (eg. acetone or methyl ethyl ketone). The hydrogenation can advantageously be carried out in the presence of an acid (eg. acetic acid or boric acid).

Furylcarbinols of the general formula Ia, where $R^6$ is cyano, alkyl, alkenyl, haloalkenyl or alkynyl of not more than 6 carbon atoms or a carboxamide group, are advantageously obtained if the furylcarbinols Ib in which $R^6$ is hydrogen are initially oxidized to the corresponding furancarbaldehydes Ic

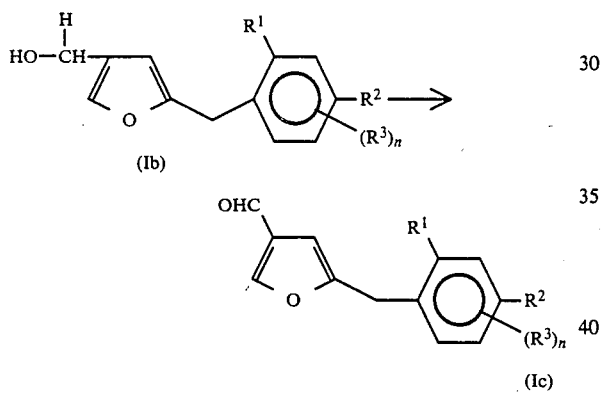

which are also novel substances.

Suitable oxidizing agents are all conventional ones which convert primary alcohols to aldehydes but are not so highly acidic that cleavage of the furan ring occurs (Houben-Weyl, Methoden der Organischen Chemie, Volume E3, page 265 et seq.). Compounds containing transition metals in a fairly high oxidation state, eg. pyridine dichromate, are particularly suitable.

The furancarbaldehydes are converted back to the furylcarbinols, which now carry a substituent $R^6$, in a subsequent reaction step. To do this, (a) where $R^6$ is cyano, the furancarbaldehyde is reacted in a conventional manner with hydrocyanic acid (or a metal cyanide in the presence of an acid), ie. is subjected to the cyanohydrin reaction, and (b) where $R^6$ is alkyl, alkenyl, haloalkenyl or alkynyl, the furancarbaldehyde is reacted with an appropriate organometallic compound $R^6$—M.

Alkali metal cyanides, eg. sodium cyanide or potassium cyanide, are preferably used as the metal cyanides, and, if necessary, an auxiliary, eg. $NaHSO_3$, or a phase-transfer catalyst is added to the two-phase system.

Suitable organometallic compounds are those containing metals of main group 1 and the corresponding Grignard compounds, the latter, eg. vinylmagnesium chloride, being preferred because they are easier to handle.

The present invention furthermore relates to a process for the preparation of the isoxazolines which are required as intermediates and are of the general formula IV

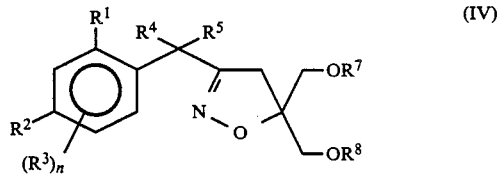

where $R^1$ to $R^5$ have corresponding meanings and $R^7$ and $R^8$ are identical or different and are each, for example, hydrogen, alkyl, alkylcarbonyl, arylcarbonyl or another hydroxyl-protective group which can be eliminated. $R^7$ and $R^8$ are obviously only present as aids.

The isoxazolines are advantageously prepared starting from the corresponding phenylacetaldehydes V. These can be converted with hydroxylamine or a hydroxylammonium salt in the presence of an assistant, eg. a base, to oximes IV

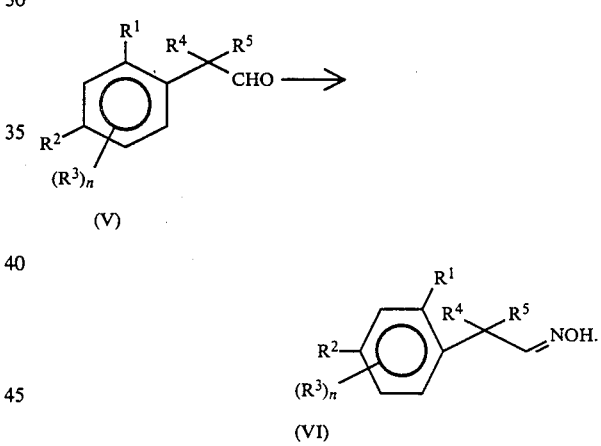

By means of well known methods (The Nitrile Oxides by Grundmann, Grüanger, 1st edition 1971, page 96 et seq.), the oximes can be converted to nitrile oxides (VII), which can be reacted with olefines VIII to give the desired isoxazolines [also see Heterocycles, 12 (1979), 1243 et seq.; Houben-Weyl, Methoden der Organischen Chemie, 14th edition, Volume 10/3, page 837, Stuttgart 1965]:

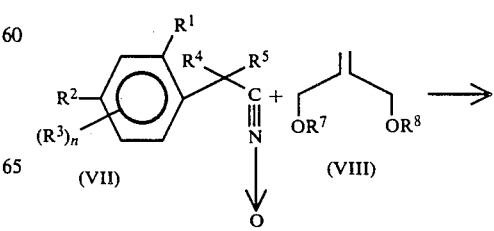

37 g of 3-hydroxymethyl-5-(p-fluorobenzyl)-furan in 100 ml of pyridine is added dropwise, likewise at 0° C., and the mixture is stirred for 2 hours at room temperature and left to stand in this temperature for some time. The dark reaction mixture is added to 3000 ml of water, and the solution is extracted several times with ether. The combined ether solutions are washed with dilute hydrochloric acid and then with water, dried over sodium sulfate and evaporated down.

Purification by column chromatography over silica gel using toluene as an eluent gives 23 g of 3-formyl-5-(p-fluorobenzyl)-furan ($n_D^{22}$: 1.5415).

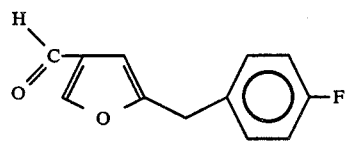

250 MHz NMR spectrum in $CDCl_3$: $\delta[ppm] = 3.95$ (2H), 6.39 (1H), 6.94–7.05 (2H), 7.13–7.23 (2H), 7.95 (1H), 9.86 (1H).

6. Preparation example for a furylcarbinol ($R^6 \neq H$)

46.5 ml of a 1.5M solution of vinylmagnesium chloride in tetrahydrofuran are initially taken in 60 ml of absolute tetrahydrofuran at 0° C. 11.9 g of 3-formyl-5-(p-fluorobenzyl)-furan in 60 ml of absolute tetrahydrofuran are added dropwise at 0°–10° C. to the stirred mixture in the absence of moisture, and stirring is continued for 15 hours at room temperature. 100 ml of a saturated ammonium chloride solution and 20 ml of glacial acetic acid are added carefully to the reaction mixture, the precipitate dissolving. The mixture is extracted three times by shaking with ether, after which the combined ether extracts are washed with water, dried over sodium sulfate and evaporated down under reduced pressure. The oil obtained (14 g) is purified by column chromatography over silica gel using toluene/acetone (9/1) as the eluent. 7.1 g of 3-(1-hydroxy-2-propenyl)-5-(p-fluorobenzyl)-furan are obtained as an oil ($n_D^{22}$: 1.5370).

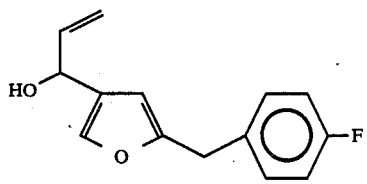

200 MHz NMR spectrum in $CDCl_3$: $\delta[ppm] = 1.87$ (1H, broad), 3.93 (2H), 5.07–5.43 (1H, 1H, 1H), 5.97–6.17 (1H, 1H), 6.94–7.08 (2H), 7.16–7.33 (2H, 1H).

TABLE 1

| | | | | | | Oximes | |
|---|---|---|---|---|---|---|---|
| $R^1$ | $R^2$ | $R^3$ | $R^4$ | R | Melting point [°C.] | Measurement frequency [MHz] | $^1H$ NMR data ($CDCl_3$) $\delta[ppm]$ |
| H | H | H | $CH_3$ | H | oil | 270 | cis/trans isomer mixture: 1.45 (2H), 3.68 and 4.46 (1H), 6.82 and 7.52 (1H), 7.18–7.38 (5H) |
| F | H | H | H | H | | 300 | cis/trans isomer mixture: 3.57 and 3.76 (2H), 6.86 and 7.53 (1H), 6.9–7.3 (4H) |
| H | H | 3-F | H | H | | 300 | cis/trans isomer mixture: 3.5 and 3.74 (2H), 6.7–7.38 (4H), 7.5 and 7.64 (1H), 8.3 and 8.83 (1H, broad) |
| Cl | H | 6-F | H | H | | 300 | cis/trans isomer mixture: 3.72 and 3.91 (2H), 6.72 and 7.52 (1H), 7.01 (1H), 7.2 (2H) |
| Cl | H | H | H | H | | 300 | cis/trans isomer mixture: 3.66 and 3.85 (2H), 6.86 and 7.57 (1H), 7.22 (3H), 7.37 (1H) |
| H | H | 3-Cl | H | H | 65–73 | 300 | cis/trans isomer mixture: 3.52 and 3.73 (2H), 6.88 and 7.52 (1H), 7.1 (1H), 7.23 (3H), 9.22 and 9.7 (1H, broad) |
| Cl | Cl | H | H | H | 103–110 | 270 | cis/trans isomer mixture: 3.63 and 3.8 (2H), 6.85 and 7.55 (1H), 7.13–7.28 (2H), 7.4 (1H), 8.35 and 8.92 (1H, broad) |
| H | $OCH_3$ | 3-$OCH_3$ | H | H | 80–87 | 200 | cis/trans isomer mixture: 3.53 and 3.75 (2H), 3.93 (6H), 6.75–6.9 (3H), 6.95 and 7.6 (1H) |
| H | H | 3-$CF_3$ | H | H | | 300 | cis/trans isomer mixture: 3.58 and 3.79 (2H), 6.87 and 7.67 (1H), 7.3–7.62 (4H) |

TABLE 2

| | | Isoxazolines | | | | | Measurement frequency [MHz] | $^1H$ NMR data ($CDCl_3$) $\delta[ppm]$ |
|---|---|---|---|---|---|---|---|---|
| $R^1$ | $R^2$ | $R^3$ | $R^4$ | $R^5$ | $R^7$ | $R^8$ | | |
| H | H | H | $CH_3$ | H | Ac | Ac* | 300 | 1.53 (3H, doublet), 2.0 (3H), 2.03 (3H), 2.71 (2H, multiplet), 3.82 (1H, quartet), 4.12 (2H), 4.15 (2H), 7.18–7.42 (5H) |
| H | H | H | $CH_3$ | $CH_3$ | Ac | Ac | 300 | 1.6 (6H), 2.06 (6H), 2.65 (2H), 4.12 (4H), 7.17–7.44 (5H) |
| H | H | 3-F | H | H | Ac | Ac | 300 | 2.03 (6H), 2.77 (2H), 3.68 (2H), 4.06–4.23 (4H), 6.8–7.4 (4H) |

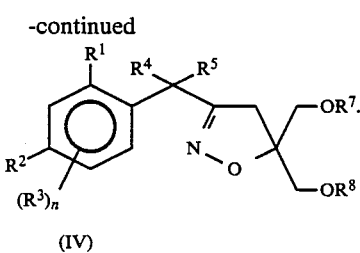

(IV)

It is not absolutely essential to isolate the nitrile oxides. They are advantageously reacted in situ with the alkenyl compounds.

The nitrile oxides used to prepare the isoxazolines, and the alkenyl compounds, can be employed in stoichiometric amounts or one of the reactants can be employed in excess.

Examples of suitable solvents for the reaction are the particular alkenyl compound itself, as well as aromatic compounds (eg. benzene, toluene or xylene), halogenated aromatic compounds, ketones (eg. acetone or methyl ethyl ketone), ethers (eg. diethyl ether, tertahydrofuran or dioxane) and chlorinated aliphatic hydrocarbons (eg. methylene chloride or chloroform).

1. Preparation example for an oxime 113 g of hydroxylammonium chloride in 300 ml of water are added to 160 g of p-fluorophenylacetaldehyde in 500 ml of methylene chloride. A solution of 87 g of sodium carbonate in 300 ml of water is slowly added dropwise to the stirred mixture at room temperature, and the reaction is allowed to continue for 2 days. The organic phase is separated off, washed with water, dried over $Na_2SO_4$ and filtered, and the filtrate is freed from the solvent. 161 g of p-fluorophenylacetaldoxime of melting point 113°–115° C. are obtained. 200 MHz NMR spectrum in $CDCl_3$:

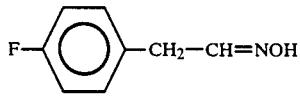

(cis/trans isomer mixture=1:1)

$\delta[ppm]=3.51$ and 3.72 (2 doublets, 2H, J=7 Hz, $CH_2$), 6.9 and 7.54 (2 triplets, 1H, J=7 Hz, =CH), 6.95–7.32 (4H, aromatic protons) 8.52 and 9.02 (1H, OH)

2. Preparation example for an isoxazoline

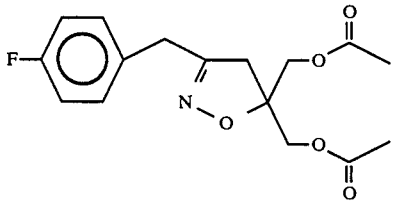

203.5 g of p-fluorophenylacetaldoxime and 255 g of 2-methylenepropane-1,3-diol diacetate are dissolved in 1000 ml of diethyl ether. 1000 ml of a 10% strength sodium hypochlorite solution are slowly added dropwise at 20°–30° C. (cooling), while stirring vigorously. After stirring has been continued for 20 hours, the organic phase is separated off, washed with water and dried over sodium sulfate, and the solvent is stripped off. Excess isobutylene diacetate is distilled off over a bridge (bp. 70° C./mm Hg). 312 g of 3-(p-fluoroebenzyl)-5,5-bis-acetoxymethyl-isoxazoline are obtained in the form of a viscous oil.

300 MHz NMR spectrum in $CDCl_3$: $\delta[ppm]=2.03$ (6H, 2×$OCH_3$), 2.75 (2H, $CH_2$), 3.65 (2H, $CH_2$), 4.15 (4H, 2×$OCH_2$), 6.95–7.1 (2H, aromatic protons), 7.15–7.3 (2H, aromatic protons), 3. Example of the elimination of the protective groups on the isoxazoline A solution of 58.3 g of KOH in 900 ml of ethanol is added to 138 g of 3-(p-fluorobenzyl)-5,5-bis-(acetoxymethyl)-isoxazoline, and the mixture is refluxed for 12 hours. After the mixture has been cooled, the precipitated salt is filtered off and the solvent is removed under reduced pressure. Acetone is added, after which precipitated solid is again filtered off under suction and the filtrate is evaporated down. The oil obtained can be purified by column chromatography [silica gel; eluent: toluene/acetone (initially 9/1, subsequently 1/1)]. 83 g of 3-(p-fluorobenzyl)-5,5-bis-(hydroxymethyl)-isoxazoline of melting point 93°–97° C. are obtained.

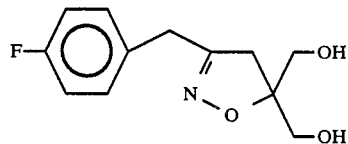

Analysis: Calculated: C 60.20, H 5.9, N 5.85, F 7.94; Found: C 60.3, H 5.6, N 5.9, F 8.0

270 MHz NMR specturm in $CDCl_3$: $\delta[ppm]=2.3$ (2H, OH, broad), 2.8 (2H), 3.5–3.75 (2H, 2H, 2H), 6.95–7.25 (4H)

4. Preparation example for a furylcarbinol ($R^6$=H)

67.9 g of 3-(p-fluorobenzyl)-5,5-bis-(hydroxymethyl)-isoxazoline are taken up in 400 ml of tetrahydrofuran, 80 ml of glacial acetic acid and 40 ml of water, and 1.5 g of platinum(IV) oxide hydrate are added. Hydrogenation is carried out for 5–6 hours at 25°–30° C., a slightly exothermic reaction taking place (cooling). When the absorption of hydrogen is complete, the catalyst is filtered off, the filtrate is evaporated down and the residue is stirred in 400 ml of methylene chloride with 400 ml of 10% strength hydrochloric acid for 1 hour at room temperature. The organic phase is separated off, washed neutral, dried over sodium sulfate and evaporated down. Purification by column chromatography over silica gel with toluene/acetone 9/1 as the eluent gives 37 g of 3-hydroxymethyl-5-(p-fluorobenzyl)-furan of melting point 45°–47° C.

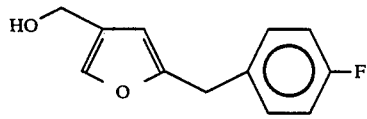

Analysis: Calculated: C 69.89, H 5.38, F 9.21; Found: C 69.2, H 5.6, F 9.2.

250 MHz NMR spectrum in $CDCl_3$: $\delta[ppm]=2.1$ (1H, broad), 3.87 (2H), 4.42 (2H), 6.01 (1H), 6.97–7.0 (2H), 7.1–7.2 (2H), 7.26 (1H)

5. Preparation example for a furancarbaldehyde 59 g of chromium(VI) oxide are added a little at a time to 100 ml of pyridine at 0° C., a bulky yellow precipitate being formed. After 15 minutes, a solution of

TABLE 2-continued

| R¹ | R² | R³ | R⁴ | R⁵ | R⁶ | R⁷ | | ¹H NMR data [CDCl₃] δ[ppm] |
|---|---|---|---|---|---|---|---|---|
| Cl | Cl | H | H | H | Ac | Ac | 200 | 2.06 (6H), 2.8 (2H), 3.81 (2H), 4.16 (4H), 7.25 (2H), 7.43 (1H) |
| H | OCH₃ | 3-OCH₃ | H | H | Ac | Ac | 300 | 2.05 (6H), 2.77 (2H), 3.62 (2H), 3.89 (6H), 4.16 (4H), 6.7–6.9 (3H) |
| H | H | 3-CF₃ | H | H | Ac | Ac | 300 | 2.01 (6H), 2.8 (2H), 3.75 (2H), 4.04–4.23 (2H) (2H, 2H), 7.4–7.68 (4H) |
| H | Cl | H | H | H | Ac | Ac | 300 | 2.04 (6H), 2.75 (2H), 2.65 (2H), 4.14 (4H), 7.02–7.42 (4H) |

*Ac = Acetyl

| Isoxazolines | | | | | Melting point [°C.] | Measurement frequency [MHz] | ¹H NMR data [CDCl₃] δ[ppm] | Analysis |
|---|---|---|---|---|---|---|---|---|
| R¹ | R² | R³ | R⁴ | R⁵ | | | | |
| H | H | H | CH₃ | H | 84–85 | 200 | 1.52 (3H, doublet, J = 8 Hz), 2.6 (2H, broad), 2.7 (2H), 3.45–3.71 (4H), 3.78 (1H, quartet, J = 8 Hz), 7.18–7.42 (5H) | Calc. C 66.36 H 7.28 O 20.4 N 5.95 Found C 66.4 H 7.3 O 20.6 N 5.9 |
| H | H | H | CH₃ | CH₃ | | 300 | 1.57 (6H), 2.65 (2H), 3.26 (2H, broad) 3.47–3.68 (2H, 2H), 7.14–7.43 (5H) | Calc. C 67.5 H 7.7 N 5.6 Found C 67.3 H 7.6 N 5.5 |
| F | H | H | H | H | | 300 | *2.72 (2H), 3.35 (4H), 3.65 (2H), 4.99 (2H, broad), 7.1–7.4 (4H) | |
| H | H | 3-F | H | H | | 300 | 2.78 (2H), 3.1 (2H, broad), 3.48–3.71 (6H), 6.86–7.03 (3H), 7.2–7.35 (1H) | |
| Cl | H | 6-F | H | H | | 200 | 2.72 (2H, broad), 2.9 (2H), 3.53–3.73 (2H, 2H), 3.87 (2H), 6.97–7.11 (1H), 7.19–7.3 (2H) | |
| Cl | H | H | H | H | | 200 | 2.7 (2H, broad), 2.85 (2H), 3.52–3.77 (2H, 2H), 3.83 (2H), 7.2–7.48 (4H) | |
| H | H | 3-Cl | H | H | Oil | 270 | 2.8 (2H), 2.9 (2H, broad) 3.5–3.71 (2H, 2H, 2H), 7.05–7.35 (1H, 3H) | Calc. C 56.37 H 5.52 O 18.77 N 5.48 Cl 13.86 Found C 57.5 H 5.8 O 18.2 N 5.4 Cl 13.4 |
| Cl | Cl | H | H | H | 102–111 | 300 | 2.1 (2H, broad), 2.86 (2H) 3.58 (2H), 3.71 (2H), 3.78 (2H), 7.23 (2H), 7.41 (1H) | |
| H | OCH₃ | 3-OCH₃ | H | H | 105–108 | 270 | 2.75 (2H), 3.6 (4H, 2H), 3.82 (6H), 6.65–6.84 (3H) | Calc. C 59.78 H 6.81 O 28.44 N 4.98 Found C 60.2 H 6.8 O 28.7 N 4.6 |
| H | H | 3-CF₃ | H | H | | 270 | 2.42 (1H, broad), 2.81 (2H), 3.51–3.75 (2H, 2H, 2H), 7.37–7.59 (4H) | |
| H | Cl | H | H | H | | 300 | 2.5 (2H, broad), 2.79 (2H), 3.5–3.7 (2H, 2H, 2H), 7.13–7.22 (2H), 7.25–7.35 (2H) | |

R⁷, R⁸ = H
*recorded in DMSO-d₆

TABLE 3

| Furylcarbinols | | | | | | Refractive index | frequency [MHz] | Measurement ¹H NMR data [CDCl₃] δ[ppm] | Analysis |
|---|---|---|---|---|---|---|---|---|---|
| R¹ | R² | R³ | R⁴ | R⁵ | R⁶ | | | | |
| H | H | H | CH₃ | H | H | $n_D^{24}$: 1.5467 | 200 | 1.56 (3H, doublet, J = 7Hz), 2.05 (1H, broad), 4.06 (1H, quartet, J = 7Hz), 4.43 (2H), 6.1 (1H), 7.15–7.38 (5H,1H), | Calc. C 77.2 H 6.98 O 15.82 Found C 76.5 H 7.20 O 16.6 |
| H | H | H | CH₃ | CH₃ | H | | 360 | 1.39 (6H), 2.72 (1H, broad), 4.23 (2H), 5.91 (1H), 6.88–7.15 (5H, 1H) | |
| F | H | H | H | H | H | | 300 | 2.32 (1H, broad), 3.95 (2H), 4.42 (2H), 6.04 (1H), 6.97–7.27 (4H, 1H) | |
| H | H | 3-F | H | H | H | | 300 | 3.25 (1H, broad), 3.92 (2H), 4.45 (2H), 6.06 (1H), 6.84–7.05 (3H), 7.19–7.34 (1H,1H) | |
| Cl | H | 6-F | H | H | H | | 300 | 1.92 (1H, broad), 4.11 (2H), 4.43 (2H), 6.02 (1H), 6.95–7.05 (1H), 7.12–7.23 (2H), 7.27 (1H) | |

TABLE 3-continued

| Furylcarbinols | | | | | | Refractive index | frequency [MHz] | Measurement $^1$H NMR data [CDCl$_3$] $\delta$[ppm] | Analysis | |
|---|---|---|---|---|---|---|---|---|---|---|
| R$^1$ | R$^2$ | R$^3$ | R$^4$ | R$^5$ | R$^6$ | | | | | |
| Cl | H | H | H | H | H | | 300 | 2.05 (1H, broad), 4.04 (2H), 4.43 (2H), 6.04 (1H), 7.17 (3H), 7.27 (1H), 7.3–7.38 (1H) | | |
| H | H | 3-Cl | H | H | H | n$_D^{22}$: 1.5631 | 200 | 1.73 (1H, broad), 3.9 (2H), 4.47 (2H), 6.06 (1H), 7.05–7.25 (4H), 7.3 (1H) | Calc. Found | C 64.73 H 4.98 O 14.37 Cl 15.9 C 65.3 H 5.0 O 15.0 Cl 15.1 |
| Cl | Cl | H | H | H | H | | 200 | 2.26 (1H, broad), 4.03 (2H), 4.47 (2H), 6.07 (1H), 7.15 (2H), 7.31 (1H), 7.4 (1H) | Calc. Found | C 56.06 H 3.92 O 12.45 Cl 27.58 C 56.0 H 4.0 O 12.6 Cl 27.5 |
| H | OCH$_3$ | 3-OCH$_3$ | H | H | H | 62–64 | 200 | 2.1 (1H, broad), 3.83 (6H), 3.87 (2H), 4.47 (2H), 6.03 (1H), 6.79 (3H), 7.28 (1H) | | |
| H | H | 3-CF$_3$ | H | H | H | | 300 | 3.98 (2H), 4.48 (2H), 6.07 (1H), 7.3 (1H), 7.33–7.6 (4H) | | |
| H | F | H | H | H | —C≡CH | | 200 | 2.26 (1H), 2.57 (1H), 3.93 (2H), 5.33 (1H), 6.13 (1H), 6.93–7.07 (2H), 7.14–7.27 (2H), 7.44 (1H) | | |

By appropriately modifying the preparation methods, it is possible to obtain, for example, the following furylcarbinols:

TABLE 4

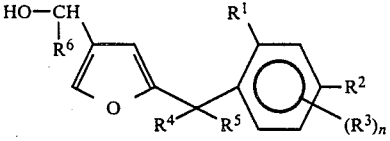

| R$^1$ | R$^2$ | R$^3$ | n | R$^4$ | R$^5$ | R$^6$ |
|---|---|---|---|---|---|---|
| H | F | H | — | H | H | CH$_3$ |
| H | F | H | — | CH$_3$ | H | H |
| H | F | H | — | H | H | CH(CH$_3$)$_2$ |
| H | F | H | — | C$_2$H$_5$ | C$_2$H$_5$ | H |
| H | F | H | — | H | H | CN |
| H | F | H | — | H | H | n-C$_4$H$_9$ |
| H | F | H | — | H | H | CF=CF$_2$ |
| H | H | 3-F | 1 | H | H | CN |
| H | H | 3-F | 1 | H | H | C≡CH |
| H | F | 3-Cl | 1 | H | H | H |
| H | tert.-C$_4$H$_9$ | H | — | H | H | C$_2$H$_5$ |
| H | CF$_3$ | H | — | H | H | H |
| CF$_3$ | H | H | — | H | H | H |
| H | CF$_3$ | H | — | H | H | CN |
| H | CF$_3$ | H | — | H | H | C=CH |
| H | F | 3-CF$_3$ | 1 | H | H | H |
| F | F | H | — | H | H | H |
| H | Cl | 3-Cl | 1 | H | H | CN |
| Cl | Cl | H | — | H | H | C≡CH |
| H | H | Cl(3,5) | 2 | H | H | C=CH$_2$ |
| F | F | F | 3 | H | H | H |
| F | F | F | 3 | H | H | C≡CH |
| H | F | 3F | 1 | H | H | H |
| H | H | 3F | 1 | H | H | CN |
| H | n-C$_4$H$_9$ | H | — | CH(CH$_3$)$_2$ | H | H |
| C$_2$H$_5$ | C$_2$H$_5$ | H | — | CH$_3$ | CH$_3$ | CH$_3$ |
| H | OCF$_3$ | H | — | H | H | H |
| H | OCF$_3$ | H | — | H | H | CN |
| H | OCF$_3$ | H | — | H | H | CH=CH$_2$ |
| H | OCHF$_2$ | H | — | H | H | H |
| OCH$_3$ | OCH$_3$ | 3-OCH$_3$ | 1 | H | H | CF=CF$_2$ |
| F | H | H | — | H | H | CH(CH$_3$)$_2$ |
| H | SCF$_3$ | H | — | H | H | H |
| Cl | Cl | Cl(3,5) | 2 | H | H | H |
| H | CH=Cl$_2$ | H | — | H | H | H |
| H | H | CH$_2$—CH=CH$_2$ (3,5) | 2 | H | H | CH=CH$_2$ |
| Br | H | H | — | H | H | CH(CH$_3$)$_2$ |

TABLE 4-continued

| R¹ | R² | R³ | n | R⁴ | R⁵ | R⁶ |
|---|---|---|---|---|---|---|
| H | O—tert.-C₄H₉ | H | — | H | H | H |
| H | OCH₃ | 3-Br | 1 | H | H | CN |
| H | OCF₂—CHF₂ | H | — | H | H | H |
| H | O—(CH₂)₅—CH₃ | H | — | H | H | CH₃ |
| F | F | H | — | H | H | CN |
| H | F | 3-CH₃ | 1 | H | H | H |
| H | H | H | — | CH(CH₃)₂ | H | CH(CH₃)₂ |
| F | H | 6-F | 1 | H | H | H |
| H | OCH₃ | OCH₃(3,5) | 2 | H | H | H |
| F | H | H | — | H | H | C≡CH |
| F | H | H | — | H | H | CN |
| Cl | H | 6-F | 1 | H | H | CN |

Regarding the preparation of the novel active ingredients (pyrethroids; ie. esters) the following may be stated:

The benzylfurylcarbinols described above are esterified with typical pyrethroid carboxylic acids; these acids and their derivatives are described in, for example, Wegler, Chemie der Pflanzenschutz- und Schälingsbekämpfungsmittel, Volume 7, Springer Verlag, Berlin, Heidelberg, New York 1981.

Typical carboxylic acids of the formula A—OH are stated in the list below. This list is not intended to imply any restriction.

A 1: 2-(2',2'-dimethylvinyl)-3,3-dimethylcyclopropane-1-carboxylic acid

A 2: 2-(2',2'-dichlorovinyl)-3,3-dimethylcyclopropanecarboxylic acid

A 3: 4-chlorophenylisovaleric acid

A 4: 4-fluorophenylisovaleric acid

A 5: 4-difluoromethoxyisovaleric acid

A 6: 2-(4'-tert-butylphenyl)-3,3-dimethylcyclopropanecarboxylic acid

A 7: 2,2,3,3-tetramethylcyclopropanecarboxylic acid

A 8: 2-(2'-trifluoromethyl-2'-chlorovinyl)-3,3-dimethylcyclopropanecarboxylic acid A 9: 2-(2',2'-dibromovinyl)-3,3-dimethylcyclopropanecarboxylic acid A 10: 2-(2'-trifluoromethyl-2'-fluorovinyl)-3,3-dimethylcyclopropanecarboxylic acid A 11: 2-(2'-methyl-2'-methoxycarbonylvinyl)-3,3-dimethylcyclopropanecarboxylic acid A 12: 2-(2',2'-difluorovinyl)-3,3-dimethylcyclopropanecarboxylic acid A 13: 1-(4'-chlorophenyl)-cyclopropane-1-carboxylic acid A 14: 1-(4-ethoxyphenyl)-2,2-dichlororcyclopropane-1-carboxylic acid A 15: 2-[2'-(4"-chlorophenyl)-2'-chlorovinyl]-3,3-dimethylcyclopropanecarboxylic acid A 16: 2-(2'-vinylvinyl)-3,3-dimethylcyclopropanecarboxylic acid A 17: 2-(2',2'-biatrifluoromethylvinyl)-3,3-dimethylcyclopropanecarboxylic acid A 18: 2-(4'-trifuloromethyl-2'-chlorophenylamino)-3-methylbutyric acid A 19: 1,1-dimethyl-2,2[H]indenespirocyclopropane-3-carboxylic acid A 20: 2-cyclopentylidenemethyl-3,3-dimethylcyclopropanecarboxylic acid A 21: [dihydro-2-oxo-3-(2H)-thienylidenemethyl]-2,2-dimethylcyclopropane-1-carboxylic acid A 22: 2-(2'-chloro-4'-trifluoromethylphenyl)-aminoisovaleric acid.

Of course, the compounds of the formula I occur in each case in the form of pure diastereomers, with one or more pairs of optical antipodes, and in many cases also in the form of several disatereomers. The said compounds can be used as active ingredients, which, depending on the starting materials and the reaction conditions, are obtained in pure form or as mixtures. The mixtures can be separated into their sterically pure components in a conventional manner; their biological action in specific cases is dependent on their steric configuration.

The novel esters of the formula I can be prepared by appropriately modifying the examples below.

PREPARATION EXAMPLE 1

2-(2'-Chloro-6'-fluorobenzyl)-4-methyl-furyl 2-(2',2'-dibromovinyl)-3,3-dimethylcyclopropane-1-carboxylate (A 9 ester)

6.45 g of 2-(2',2'-dibromovinyl-3,3-dimethylcyclopropanecarboxylic acid chloride are added dropwise, at 0° to 15° C., to 4.9 g of 2-chloro-6-fluorobenzylfurylcarbin-4-ol and 2.5 g of triethylamine in 100 ml parts of toluene. When the exothermic reaction has died down, the mixture is stirred for 5 hours at 50° C. After cooling, the mixture is filtered and the toluene phase is washed with water and dried over sodium sulfate. The solvent is stripped off and the residue is subjected to incipient distillation at 60° C. 10.5 g (99% yield) of a pale yellow oil are obtained.

300 MHz NMR spectrum (ppm, CDCl₃: 1.07 (3H), 1.12 (3H), 1.31 (1H), 2.08 (1H), 4.06 (2H), 4.97 (2H), 6.02 (1H), 6.08 (1H), 6.8–7.18 (3H+1H)

PREPARATION EXAMPLE 2

2-(4'-Fluorobenzyl)-4-cyanomethylfuryl 2-(2',2'-dibromovinyl)-3,3-dimethylcyclopropane-1-carboxylate (A 9 ester)

A solution of 0.8 g of potassium cyanide in 10 ml of water and 3.5 g of 2,2-dimethyl-4-(2',2'-dibromovinyl)-cyclopropanecarboxylic acid chloride are added to 2 g of 3-formyl-5-(4'-fluorobenzyl)-furan in 50 ml of ether.

Thereafter, the mixture is stirred for 15 hours at room temperature, and the organic phase is separated off, washed with water, dried over sodium sulfate and freed from the solvent to give 4.9 g of an oil which, after purification by column chromatography, gives 2.2 g of pure compound.

200 MHz NMR spectrum in CDCl$_3$; ppm values: 1.1–1.4 (6H), 1.8 (1H), 2.15 (1H), 3.95 (2H), 6.16 (1H), 6.3 (1H), 6.2–6.75 (1H), 6.95–7.7 (5H).

The novel esters which are mentioned in the table below and for which physical properties are specified were prepared by the methods described; the other compounds in the table can readily be obtained using appropriate starting materials.

| No. | A | R$^6$ | R$^4$ | R$^5$ | R$^1$ | R$^2$ | R$^3$ | n | NMR data (MHz, 2 M) ppm |
|---|---|---|---|---|---|---|---|---|---|
| 3 | A 2 | H | H | H | Cl | H | 2-F | 1 | (300, CDCl$_3$) 1.05–1.4 (6H); 1.6–1.9 (1H); 1.95–2.4 (1H); 4.15 (2H); 4.9 (2H); 5.6–6.25 (1H + 1H); 7.0 (1H); 7.1–7.4 (3H) |
| 4 | A 9 | H | H | H | Cl | H | H | 0 | (300, CDCl$_3$) 1.18 (3H); 1.25 (3H); 1.65 (1H); 2.18 (1H); 4.06 (2H); 4.95 (2H); 6.05 (1H); 6.17 (1H); 7.06–7.4 (4H + 1H) |
| 5 | A 8 | H | H | H | H | F | H | 0 | |
| 6 | A 8 | H | H | H | H | F | 3-F | 1 | |
| 7 | A 3 | H | H | H | Cl | H | H | 0 | (300, CDCl$_3$) 0.66 (3H); 0.98 (3H); 2.28 (1H); 3.15 (1H); 4.02 (2H); 4.8–5.0 (1H + 1H); 5.95 (1H); 7.05–7.4 (10H) |
| 8 | A 19 | H | H | H | H | F | H | 0 | |
| 9 | A 20 | H | H | H | H | F | 3-F | 1 | |
| 10 | A 2 | H | H | H | Cl | H | H | 0 | (300, CDCl$_3$) 1.1–1.4 (6H); 1.6–1.81 (1H); 1.95–2.3 (1H); 1.05 (2H); 4.9 (2H); 5.6–6.25 (1H); 6.05 (1H); 7.1–7.4 (5H) |
| 11 | A 21 | H | H | H | H | F | 3-F | 1 | |
| 12 | A 22 | H | H | H | Cl | Cl | H | 0 | |
| 13 | A 1 | H | H | H | Cl | H | H | 0 | (300, CDCl$_3$) 1.1–1.3 (6H); 1.4 (1H); 1.7 (6H); 1.8–2.1 (1H); 4.05 (2H); 5.86 (2H); 4.8–5.4 (1H); 6.05 (1H); 7.11–7.4 (6H) |
| 14 | A 1 | H | H | H | H | H | 3-CF$_3$ | 0 | (300, CDCl$_3$) 1.1–1.4 (6H) 1.7 (6H); 1.8–2.2 (1H); 4.0 (2H); 4.86 (2H); 4.95–5.4 (1H); 6.08 (1H); 7.2–7.6 (5H) |
| 15 | A 2 | H | CH$_3$ | CH$_3$ | H | H | H | 0 | (200, CDCl$_3$) 1.15–1.3 (6H); 1.6–1.7 (6H); 1.7–2.4 (1H + 1H); 4.95 (2H); 5.6–6.35 (1H + 1H); 7.15–7.4 (6H) |
| 16 | A 2 | H | H | H | H | F | H | 0 | (360, CDCl$_3$) 1.1–1.4 (6H); 1.5–2.2 (2H); 3.9 (2H); 4.9 (2H); 5.6–6.3 (1H); 6.05 (1H); 6.9–7.3 (5H) |
| 17 | A 2 | H | H | H | H | H | 3-CF$_3$ | 0 | (300, CDCl$_3$) 1.08–1.2 (6H); 1.58–1.86 (1H); 1.98–2.3 (1H); 4.0 (2H); 4.93 (2H); 5.6 6.15 (1H); 6.04 (1H); 7.25–7.6 (5H) |
| 18 | A 10 | H | H | H | CF$_3$ | H | H | 0 | |
| 19 | A 8 | H | H | H | H | CF$_3$ | H | 0 | |
| 20 | A 22 | H | H | H | CF$_3$ | H | H | 0 | |
| 21 | A 1 | H | H | H | H | H | 3-F | 1 | (300, CDCl$_3$) 1.05–1.33 (6H); 1.6–1.8 (6H); 1.86 (1H); 2.07 (1H); 3.94 (2H); 4.9 (2H); 4.9–5.4 (1H); 6.05 (1H); 6.8–7.4 (5H) |
| 22 | A 9 | H | H | H | H | Cl | H | 0 | (200, CDCl$_3$) 1.5–1.3 (6H); 2.15 (1H); 2.4 (1H); 3.9 (2H); 4.9 (2H); 6.05 (1H); 6.1–6.5 (1H); 7.1–7.4 (5H) |
| 23 | A 2 | H | H | H | H | Cl | H | 0 | (200, CDCl$_3$) 1.1–1.4 |

-continued

| No. | A | R⁶ | R⁴ | R⁵ | R¹ | R² | R³ | n | NMR data (MHz, 2 M) ppm |
|---|---|---|---|---|---|---|---|---|---|
| | | | | | | | | | (6H); 1.78 (1H); 2.2 (1H); 3.9 (2H); 4.92 (2H); 5.6–6.2 (1H); 6.05 (1H); 7.1–7.4 (5H) |
| 24 | A 2 | H | H | H | F | H | H | 0 | (360, CDCl₃) 1.05–1.35 (6H); 1.7 (1H); 2.1 (1H); 3.95 (2H); 4.9 (2H); 5.5–6.3 (1H); 6.1 (1H); 6.9–7.4 (5H) |
| 25 | A 1 | H | CH₃ | CH₃ | H | H | H | 0 | (300, CDCl₃) 1.15 (3H); 1.22 (3H); 1.55–1.8 (13H); 1.99 (1H); 4.9 (2H); 6.18 (1H); 7.1–7.4 (6H) |
| 26 | A 9 | H | CH₃ | CH₃ | H | H | H | 0 | (300, CDCl₃) 1.2 (3H); 1.25 (3H); 1.57–1.75 (7H); 2.1 (1H); 4.95 (2H); 6.17 (1H); 6.18–6.8 (1H); 7.1–7.4 (6H) |
| 27 | A 1 | H | H | H | H | F | H | 0 | (360, CDCl₃) 1.0–1.3 (6H); 1.7–1.9 (6H); 1.95 (1H); 2.35 (1H); 3.9 (2H); 4.9 (2H); 4.9–5.4 (1H); 6.05 (1H); 6.9–7.4 (5H) |
| 28 | A 1 | H | H | H | F | H | H | 0 | (360, CDCl₃) 1.0–1.25 (6H); 1.6–1.8 (6H); 1.85 (1H); 2.0 (1H); 3.9 (2H); 4.85 (2H); 4.9–5.3 (1H); 6.05 (1H); 6.9–7.4 (5H) |
| 29 | A 2 | H | H | H | H | H | 3-F | 1 | (360, CDCl₃) 1.0–1.4 (6H); 1.74 (1H); 2.12 (1H); 3.9 (2H); 4.9 (2H); 5.6–6.3 (1H); 6.1 (1H); 6.1 (1H); 6.8–7.3 (5H) |
| 30 | A 9 | H | H | H | H | F | H | 0 | (200, CDCl₃) 1.1–1.4 (6H); 1.77 (1H); 2.1 (1H); 3.96 (2H); 4.95 (1H); 6.05 (1H); 6.1–6.8 (1H); 6.9–7.45 (5H); |
| 31 | A 3 | H | H | H | H | F | H | 0 | (200, CDCl₃) 0.7 (3H); 1.05 (3H); 2.3 (1H); 3.17 (1H); 3.9 (2H); 4.8–5.05 (2H); 5.94 (1H); 6.95–7.35 (9H) |
| 32 | A 2 | H | H | H | H | F | 3-F | 1 | |
| 33 | A 2 | H | H | H | F | F | 3-F | 1 | |
| 34 | A 9 | H | H | H | F | F | F | 3 | |
| 35 | A 9 | H | H | H | F | F | F | 2 | |
| 36 | A 8 | H | H | H | H | F | 3-F | 1 | |
| 37 | A 9 | ethynyl | H | H | H | F | H | 0 | (300, CDCl₃) 1.1–1.4 (6H); 1.8 (1H); 2.08 (1H); 2.58 (1H); 3.92 (2H); 6.1 (1H); 6.37 (1H); 6.15–6.9 (1H); 6.95–7.5 (5H) |
| 38 | A 3 | H | H | CH₃ | H | H | H | 0 | (200, CDCl₃) 0.68 (3H), 0.99 (3H); 1.53 (3H); 2.28 (1H); 3.13 (1H); 4.04 (1H); 4.9 (2H); 5.96 (1H); 7.1–7.4 (10H) |
| 39 | A 3 | H | H | H | Cl | Cl | H | 0 | (270, CDCl₃) 0.6 (3H); 1.0 (3H); 2.3 (1H); 3.13 (1H); 3.95 (2H); 4.98 (2H); 5.95 (1H); 6.9–7.4 (8H) |
| 40 | A 9 | CN | H | H | H | F | H | 0 | (200, CDCl₃) 1.1–1.4 (6H); 1.8 (1H); 2.1 (1H); 3.95 (2H); 6.16 (1H); 6.3 (1H); 6.2–6.75 (1H); 6.95–7.7 (5H) |
| 41 | A 9 | H | H | H | Cl | Cl | H | 0 | (270, CDCl₃) 1.1–1.35 (6H); 1.62 (1H); 2.06 (1H); 4.0 (2H); 4.92 (2H); 6.05 (1H); 6.1–6.7 (1H); 7.1–7.4 (4H) |
| 42 | A 1 | H | H | H | Cl | Cl | H | 0 | (270, CDCl₃) 1.08–1.3 (6H); 1.5 (1H); 1.6–1.75 (6H); 1.97 (1H); |

-continued

| No. | A | R⁶ | R⁴ | R⁵ | R¹ | R² | R³ | n | NMR data (MHz, 2 M) ppm |
|---|---|---|---|---|---|---|---|---|---|
| 43 | A 9 | CH₂=CH— | H | H | H | F | H | 0 | 4.0 (2H); 4.86 (2H); 4.9–5.4 (1H); 6.05 (1H); 7.05–2.7 (4H) (300, CDCl₃ 1.1–1.38 (3H); 1.78 (1H); 2.05 (1H); 4.9 (2H); 4.1–4.2 (2H); 5.9–6.23 (4H); 6.91–7.37 (5H) |
| 44 | A 9 | H | H | H | H | H | 3-Cl | 1 | (300, CDCl₃) 1.1–1.4 (6H); 1.78 (1H); 2.09 (1H); 3.91 (2H); 4.92 (2H); 6.07 (1H); 6.1–6.8 (1H); 7.08–7.4 (5H) |
| 45 | A 2 | H | H | H | Cl | Cl | H | 0 | (270, CDCl₃) 1.05–1.35 (6H); 1.71 (1H); 2.1 (1H); 4.0 (2H); 4.92 (2H); 6.08 (1H); 5.04–6.3 (1H); 7.05–7.45 (4H) |
| 46 | A 1 | H | H | H | H | H | 3-Cl | 1 | (300, CDCl₃) 1.1–1.3 (6H); 1.6 (1H); 1.55–1.8 (6H); 1.95 (1H); 3.88 (2H); 4.92 (2H); 4.9–5.4 (1H); 6.05 (1H); 7.04–7.4 (5H) |
| 47 | A 3 | H | H | H | H | H | 3-Cl | 1 | (300, CDCl₃) 0.67 (3H); 1.0 (3H); 2.3 (1H); 3.17 (1H); 4.88 (2H); 4.9 (2H); 5.98 (1H); 7.02–7.38 (9H) |
| 48 | A 2 | CH₂=CH— | H | H | H | F | H | 0 | (300, CDCl₃) 1.1–1.38 (6H); 1.77 (1H); 2.16 (1H); 3.98 (2H); 5.2–5.65 (2H); 5.86–6.16 (4H); 6.9–7.35 (5H) |
| 49 | A 2 | H | H | H | H | H | 3-Cl | 1 | (300, CDCl₃) 1.1–1.3 (6H); 1.74 (1H); 2.17 (1H); 3.9 (2H); 4.9 (2H); 6.05 (1H); 5.55–6.3 (1H); 7.05–7.4 (5H) |
| 50 | A 9 | H | H | CH₃ | H | H | H | 0 | (200, CDCl₃) 1.2 (3H); 1.3 (3H); 1.67 (1H); 2.2 (1H); 4.1 (1H); 4.92 (2H); 6.1 (1H); 6.1 (1H); 6.18 (1H); 7.2–7.4 (6H) |
| 51 | A 2 | H | H | CH₃ | H | H | H | 0 | (200, CDCl₃) 1.1–1.4 (6H); 1.1 (3H), 1.92 (1H); 2.25 (1H); 4.1 (1H); 4.95 (2H); 6.1 (1H); 5.5–6.3 (1H); 7.2–7.4 (6H) |
| 52 | A 2 | HC≡C— | H | H | H | F | H | 0 | (300, CDCl₃) 1.06–1.37 (6H); 1.76 (1H), 2.17 (1H); 2.75 (1H); 3.9 (2H); 5.55–6.4 (3H); 6.95–7.52 (5H). |

USE EXAMPLES

Contact action on stable flies (*Musca domestica*), application test

1 μl of a solution of the active ingredient in acetone is applied to the ventral abdomen of 4-day old imagines lightly anesthetized with $CO_2$. A micrometer syringe is used for this purpose.

20 test animals treated in the same way are introduced into a cellophane bag (about 500 ml capacity).

After 4 hours, the number of animals which have been knocked down are counted, and the $LD_{50}$ is determined graphically.

In this test, the compounds of Examples 16, 23, 24 and 29 achieve an $LD_{50}$ of from 0.005 to 0.008 μg/fly.

The comparative agents I, II and III achieve, respectively, 0.01, 0.032 and 0.016 μg/fly. Contact action on mosquito larvae (*Aedes aegypti*)

The active ingredient preparation is added to 200 ml of tap water, and 30–40 mosquito larvae in the 4th larval stage are introduced onto the mixture.

The test temperature is 20° C. After 24 hours, the effect is determined.

In this test, the active ingredients of Examples 16, 23, 27, 29, 30, 44 and 49 achieve 100% mortality when used in concentrations from 0.002 to 0.02 ppm, whereas comparative agents I, II and III have to be used in a concentration of from 0.01 to 0.02 ppm before a similar effect is achieved. *Plutella maculipennis*; caterpillars of diamondback moths; action on ingestion and contact action Leaves of young cabbage plants are immersed for 3 seconds in the aqueous emulsion of the active ingredient, allowed to drip for a short time and then placed on a moistened filter paper in a Petri dish. 10 caterpillars in the 4th stage are then placed on the leaf.

After 48 hours, the action is assessed. In this test, the compounds of Examples 3, 4, 10, 16, 17, 21, 23, 27, 28, 29, 49, 50 and 51 have an action which is at least twice as powerful as that of comparative agent I.

We claim:

1. A 2-benzylfuryl compound of the formula I

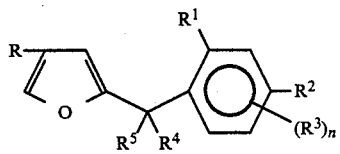

where $R^1$, $R^2$ and $R^3$ are identical or different substituents and are each hydrogen, halogen, alkyl, haloalkyl, alkoxy, haloalkoxy, haloalkylthio, alkenyl or haloalkenyl, each of not more than 6 carbon atoms, n is 1, 2 or 3 where $R^3$ is not hydrogen, $R^4$ and $R^5$ are each hydrogen or alkyl of not more than 6 carbon atoms, and R is $CHR^6OA$ in which $R^6$ is hydrogen cyano, alkyl, alkenyl, haloalkenyl or alkynyl, each of not more than 6 carbon atoms, or carboxamide, and A is an acylradical of a 3,3-dimethylcyclopropane-1-carboxylic acid substituted in the 2-position by a 2',2'-disubstituted vinyl group, the substituents in the 2'-position being selected from the group, consisting of methyl, chlorine, bromine, fluorine, trifluoromethyl, methoxycarbonyl and vinyl with the proviso that $R^2$ is not methyl, chlorine, bromine or methoxy and $R^1$ and $R^3$ are not hydrogen when A is a radical of chrysanthemumic acid and that $R^1$, $R^2$ and $R^3$ are not all hydrogen.

2. The 2-benzylfuryl compound of claim 1 wherein A is selected from the group consisting of
2-(2',2'-dimethylvinyl)-3,3-dimethylcyclopropane-1-carboxylic acid,
2-(2',2'-dichlorovinyl)-3,3-dimethylcyclopropanecarboxylic acid,
2-(2'-trifluoromethyl-2'-chlorovinyl)-3,3-dimethylcyclopropanecarboxylic acid,
2-(2',2'-dibromovinyl)-3,3-dimethylcyclopropanecarboxylic aicd,
2-(2'-trifluoromethyl-2'-fluorovinyl)-3,3-dimethylcyclopropanecarboxylic acid,
2-(2'-methyl-2'-methoxycarbonylvinyl)-3,3-dimethylcyclopropanecarboxylic acid and
2-(2',2'-difluorovinyl)-3,3-dimethylcyclopropanecarboxylic acid.

3. An insecticidal composition comprising a solution or emulsion containing an effective amount of the compound of claim 1.

4. A method of controlling insects comprising applying an effective amount of the compound of claim 1 to insects or their habitat.

* * * * *